US005676697A

United States Patent [19]

McDonald

[11] Patent Number: 5,676,697
[45] Date of Patent: Oct. 14, 1997

[54] TWO-PIECE, BIFURCATED INTRALUMINAL GRAFT FOR REPAIR OF ANEURYSM

[75] Inventor: Edward A. McDonald, Irvine, Calif.

[73] Assignee: Cardiovascular Dynamics, Inc., Irvine, Calif.

[21] Appl. No.: 681,906

[22] Filed: Jul. 29, 1996

[51] Int. Cl.⁶ .................................................. A61F 2/06
[52] U.S. Cl. ................................................... 623/1
[58] Field of Search .................................. 623/1, 11, 12; 606/194, 195

[56] References Cited

U.S. PATENT DOCUMENTS

| 3,657,744 | 4/1972 | Ersek | 3/1 |
|---|---|---|---|
| 3,826,257 | 7/1974 | Buselmaier . | |
| 4,577,631 | 3/1986 | Kreamer . | |
| 4,994,071 | 2/1991 | MacGregor | 606/194 |
| 5,100,429 | 3/1992 | Sinofsky | 606/195 |
| 5,306,286 | 4/1994 | Stack | 623/1 |
| 5,306,294 | 4/1994 | Winston et al. | 623/1 |
| 5,360,443 | 11/1994 | Barone et al. | 623/1 |
| 5,366,473 | 11/1994 | Winston et al. | 606/198 |
| 5,405,379 | 4/1995 | Lane | 623/1 |
| 5,441,515 | 8/1995 | Khosravi et al. | 606/194 |
| 5,489,295 | 2/1996 | Piplani et al. | 623/1 |
| 5,540,713 | 7/1996 | Schnepp-Pesch | 623/1 |
| 5,562,724 | 10/1996 | Vorwerk | 606/195 |
| 5,562,726 | 10/1996 | Chuter | 606/195 |

OTHER PUBLICATIONS

MinTec "Stentor" product brochure, undated, one page.
World Medical Manufacturing Corp. "Bifurcated Nitinol spring/graft" product brochure, Dec., 1995, two pages.
Corvita Corp. "Corvita Bifurcated Graft" produc brochure, undated, one page.

J. C. Parodi, M.D., et al., "Transfemoral Intraluminal Graft Implantation for Abdominal Aortic Aneurysms", *Annals of Vascular Surgery*, vol. 5, No. 6, 1991, pp. 491–499.

J. C. Parodi M.D. et al., "Endoluminal Aortic Aneurysm Repair Using a Balloon–Expandable Stent–Graft Device: A Progress Report", *Annals of Thoacic Surgery*, vol. 8, No. 6, 1994, pp. 523–529.

J. May, MS et al., "Treatment of complex abdominal aortic aneurysms by a combination of endoluminal and extraluminal aortofemoral grafts", *Journal of Vascular Surgery*, vol. 19, No. 5, 1994, pp. 924–933.

T. A. M. Chuter, M.D. et al., "Bifurcated stent–grafts for endovascular repair of abdominal aortic aneurysm", *Surgical Endoscopy*, vol. 8, 1994, pp. 800–802.

*Primary Examiner*—Michael J. Milano
*Attorney, Agent, or Firm*—Knobbe, Martens, Olson & Bear, LLP

[57] ABSTRACT

An intraluminal graft and method and apparatus for installing an intraluminal graft in relation to a bifurcation of a trunk vessel into two branch vessels to bypass an aneurysm defect or injury, wherein the intraluminal graft is formed of two cooperating graft prostheses. The first graft prosthesis is formed of a flexible tubular member having leg openings and a side, waist opening defined by self-expanding, collapsible stents that may be collapsed under restraint and positioned to bridge the bifurcation and allowed to expand to resemble trousers with the waist opening facing the lumen of trunk vessel and the legs fitting within the branch vessels and defining a first graft lumen therebetween. The second graft prosthesis is formed of a tubular member of sheet material that may be collapsed under restraint and advanced through the first graft lumen and then allowed to self-expand to be seated in the waist opening and against the trunk vessel wall.

28 Claims, 11 Drawing Sheets

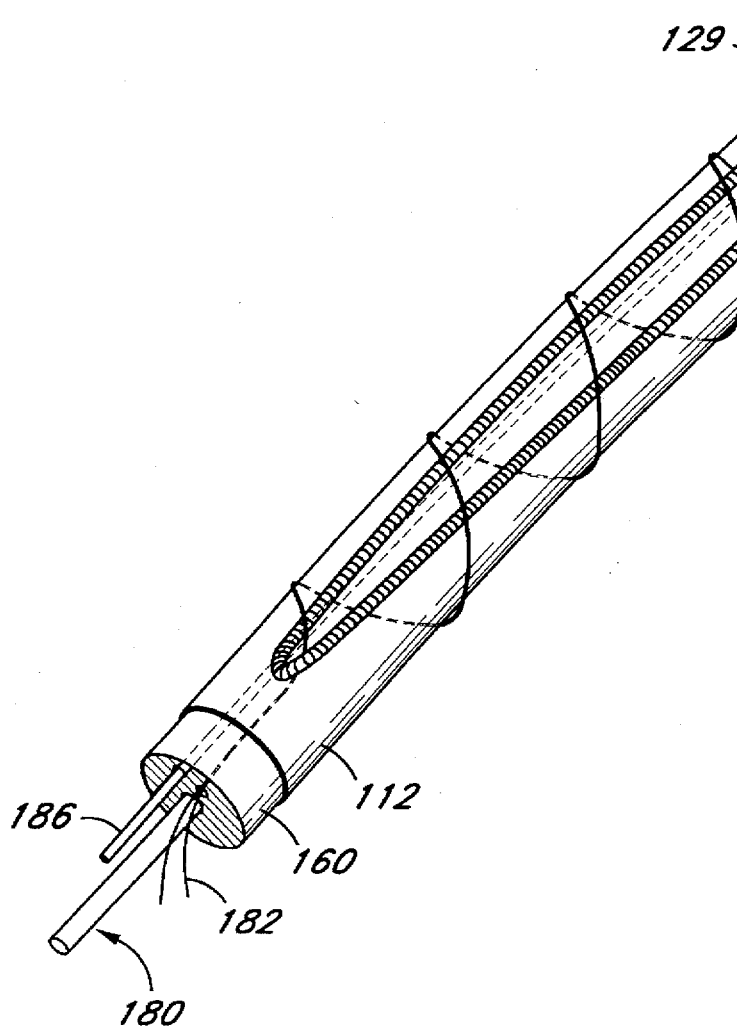

TWO-PIECE, BIFURCATED INTRALUMINAL GRAFT FOR REPAIR OF ANEURYSM

FIELD OF THE INVENTION

The present invention relates to an intraluminal graft and method and apparatus for installing an intraluminal graft in relation to a bifurcation in a body vessel that is damaged, and more particularly in relation to an aneurysm, defect or injury that affects a main body vessel, e.g., the abdominal aorta, and branching body vessels, e.g. the iliac arteries, wherein the intraluminally implanted graft is formed of two cooperating graft prostheses having a wide range of expansion when placed in position.

DESCRIPTION OF THE BACKGROUND ART

The occurrence of aneurysms in weakened blood vessel walls, particularly in arterial blood vessels, often presents a life threatening risk to a patient. This is particularly true in blood vessels serving the heart, brain and other vital organs. In arterial blood vessels, such aneurysms may rupture, causing internal bleeding and loss of blood pressure or become the source of clots that may become dislodged and are borne by moving blood to other sites where they restrict blood flow. In major arteries, the rupture may lead to severe loss of pressure and rapid death. In the brain, the pooling of blood may lead to pressure on brain cells and result in a stroke.

The invasive, surgical removal of aneurysms and/or the closure of the aneurysm opening or a rupture in the vessel wall itself presents a grave risk to the patient and poses the potential for severe post-operative complications. In patients who are otherwise relatively healthy, conventional vascular surgery or micro-surgery may be employed successfully to correct relatively small, narrow necked aneurysms of vessels accessible to such surgical approach. Surgical replacement or bypass of the vessel with grafts using sacrificed blood vessels or artificial flexible grafts has also been undertaken or proposed, particularly for vessels that are enlarged into an aneurysm encircling the vessel wall. However, the most threatening aneurysms are often deep within a vital organ or large in size and encompass a length of the vessel such that the trauma of surgical treatment presents a great risk.

It is therefore often either impossible to proceed surgically or preferable to avoid such surgical procedures. Less invasive approaches have been proposed and tested either in animals or clinically for bridging the aneurysm or filling the aneurysm sac in vessels where the proximal and distal aneurysm neck is only moderately larger than the less invasive entry site. Such an approach is much more difficult or impractical in aortic aneurysms where the neck of the aneurysm may be 5 or 6 times larger in diameter than the peripheral access vessel.

A wide variety of tubular body, artificial grafts, stents or stent-grafts have been proposed for introduction through a percutaneous access site and advancement through the vascular system to the aneurysm site and for deployment to bridge the opening and thereby close off the aneurysm. Once deployed in situ, the graft must be stabilized mechanically until neointimal growth occurs over the graft ends and interior surface. Such grafts, stents and stent-grafts have been formed of a wide variety of materials and shapes to accommodate particular vascular sites and to encourage neointimal growth. In addition, a wide variety of deployment mechanisms and techniques have been proposed to position the structure and stabilize it in place including "active" fixation mechanisms designed to penetrate the vessel wall and "passive" fixation mechanisms that press against and expand the diameter of the vessel lumen.

In this regard, expandable metal stents have been accepted in clinical use for insertion into a cardiac artery after a balloon angioplasty procedure has been employed to expand a stenosed site in order to assist in preventing re-stenosis. These stents are relatively structurally stiff, and when expanded at the site, enlarge the vessel and are passively retained in place by friction with the vessel wall. Typically, such stents are formed of wire mesh or wire looped to form a tubular member such that the inner diameter may be expanded by a balloon catheter or the like. Blood flow through the openings between wire turns is not an issue, since the wire and openings bear against the vessel wall.

Vascular grafts, on the other hand, classically have been designed to have less porous side walls, since they originally were used to bypass a diseased or enlarged blood vessel site. Moreover, the term "artificial graft" typically implies a biocompatible tubular member mimicking the flexibility of the natural blood vessel it is intended to replace. In an open chest surgical procedure, the active attachment of such flexible artificial grafts to patent blood vessel ends is effected by suturing in a procedure referred to as anastomosis.

Returning to the case of intraluminal graft implantation to bridge an aneurysm, it is similarly necessary to provide a deployment mechanism to advance the graft to the aneurysm site, and a retention mechanism to keep it there until neointimal growth stabilizes it. Certain of the retention mechanisms proposed for use with vascular grafts employ passive stent-like structures that are expanded to enlarge and frictionally engage patent vessel wall on either side of the aneurysm opening or include active barbs or hooks that are manipulated to invade the patent vessel wall and retain the graft in position. Such combinations of stent and graft structures are at times referred to as "stent-grafts". For purposes of the following disclosure and claims, the term "graft" is used to encompass any such graft, stent or stent-graft intended to be implanted intraluminally to bridge an aneurysm. The term "stent" is used in the following with respect to active and/or passive expansion and retention mechanisms for attaching ends of certain artificial intraluminal grafts, unless otherwise indicated in the drawings or description.

The simplest artificial intraluminal graft is formed as a tubular member having a continuous side wall and a single lumen that can be percutaneously advanced in a collapsed configuration and expanded to bridge the aneurysm opening. Examples of such intraluminal grafts and introduction systems are shown in U.S. Pat. Nos. 4,577,631 to Kreamer, 5,306,294 to Winston et al., 5,360,443 to Barone et al., and is described in "Transfemoral Intraluminal Graft Implantation for Abdominal Aortic Aneurysms", by J. C. Parodi M.D., et al. in *Annals of Vascular Surgery.*, vol. 5, no. 6, 1991, pp.491–499.

As noted in the above-referenced '443 patent and Parodi article, one focus of investigation and application of intraluminal grafts is to bridge abdominal aortic aneurysms that appear superiorly to the branching of abdominal aorta into the right and left iliac arteries and may extend into one or both of the iliac arteries. Where the aneurysm is confined to the wall of the abdominal artery and patent vessel wall is present superior to the branching, the simple "trunk" graft may be deployed in the manner shown in the above-referenced Parodi article.

Bifurcated grafts having one or more "legs" attached to a simple tubular graft have been proposed to bridge an aneurysm that extends into one or more of the iliac arteries as shown in certain figures of the '443 patent and in U.S. Pat. Nos. 4,994,071, 5,366,473 and 5,489,295, for example. Typically, these bifurcated grafts are formed of a single piece having a single body lumen branching into the two leg lumens to mimic the natural trunk and branch structure at the bifurcation site. The intraluminal introduction and positioning of the body and legs of the one piece graft into the proper position at the site is complicated, requiring a number of advancements and withdrawals of guide wires and catheters. Moreover, the legs and attendant leg opening stents must be folded over one another or the body, and the resulting folded graft assembled over a deployment catheter and/or within an introduction catheter is bulky and may be difficult to percutaneously introduce and advance to the site.

A further, three tubular piece, assembly is provided by the Corvita Corporation bifurcated graft. The larger tubular trunk member is implanted in the aorta first. Then the lower branch graft members are implanted one at a time in the iliac arteries. The two superior ends of the branch graft members are inserted into fittings in the lumen of the trunk member to prevent leakage of blood, and the other ends of the branch graft members are lodged in the iliac vessels so that the assembly does not slip apart. In order to insert the trunk and branch graft members, it is necessary to percutaneously advance the branch members through separate access sites through the right and left femoral arteries and the respective right and left iliac arteries.

Moreover, the resulting joint between the trunk and the branch graft members is prone to leak because of the negative seal created by placing the branch graft components inside the trunk where they oppose the flow of blood rather than outside the trunk. In addition, this negative joint may increase the amount of turbulence by creating an excessive ridge or dam over which the blood must flow. This turbulence can lead to the creation of clots which can cause emboli downstream.

Providing an effective and easily installed, bifurcated intraluminal graft for bridging an aneurysm at the branching of an iliac arteries from the abdominal aortic artery requires a graft structure that may be collapsed to a diameter of less than 15 French (5 mm) for percutaneous insertion into the femoral arteries and easy passage through the iliac arteries to the site. There, the graft must expand to the full lumen diameters of the patent arterial walls outside the length of the aneurysm to seal off and bridge the full length of the aneurysm from the infrarenal neck of the aorta to and including both iliac arteries, which typically is about 22-28 mm. The seal must be sufficiently tight to reduce blood pressure within the sealed off aneurysm. A self securing attachment mechanism with the patent arterial walls is also desirable to avoid arterial wall damage. The graft must be easily seen under fluoroscopy so that it may be located with a high degree of precision. Finally, the graft must, of course, fit a wide variety of anatomical variation, be reasonably biocompatible, and preserve normal blood flow through it.

Despite the advances made in the art as represented by the above-described bifurcated grafts and attachment methods, a need remains for an intraluminal graft and simplified method and apparatus for installing the intraluminal graft in relation to an aneurysm involving branching blood vessels, e.g., the abdominal aorta and/or iliac bifurcation, that satisfies the above requirements.

SUMMARY OF THE INVENTION

It is therefore a principal object of the present invention to provide an improved intraluminal graft that may be easily placed at relatively large or small bifurcation sites.

In a first aspect of the present invention, a two piece prosthetic graft for intraluminally bypassing an aneurysm, defect or injury in a vessel wall close to or involving a bifurcation of a trunk vessel having a trunk vessel wall and lumen into first and second branch vessels having first and second branch vessel walls and lumens, comprises: a first graft prosthesis having a continuous side wall extending a length between a first leg opening stent adapted to be expanded into contact with the first branch vessel wall and to define a first leg opening and a second leg opening stent adapted to be expanded into contact with the second branch vessel wall and to define a second leg opening, means for defining a waist opening formed in the fabric side wall along the length of the first graft prosthesis, the continuous side wall and first and second leg opening stents being expandable to an expanded state bridging the bifurcation with the waist opening adapted to be expanded and oriented to face superiorly from the bifurcation and toward the lumen of the trunk vessel to provide an attachment seat of predetermined diameter and defining a first graft lumen extending between the expanded waist lumen and the expanded first leg opening in the first branch vessel lumen and the second leg opening in the second branch vessel lumen; and a second graft prosthesis formed of tubular member having a length and a continuous side wall between distal and proximal ends and defining a second graft lumen extending between distal and proximal end openings, respectively, the tubular member having a collapsed state for advancement through one of the first and second leg openings, the first graft lumen and out the waist opening and being expandable in diameter to an expanded state when introduced superior to the bifurcation with the proximal end thereof located within the attachment seat formed by the waist opening stent, such that the expanded distal end bears against and is restrained by the trunk vessel wall beyond the area of the aneurysm, defect or injury and the proximal end bears against and is restrained by the attachment seat to seal the first and second graft lumens with the trunk vessel lumen and from the aneurysm, defect or injury.

Preferably, continuous side wall and the first and second leg opening stents of the first prosthetic graft are collapsible when restrained in a collapsed state and expandable when unrestrained to an expanded state defining the first graft lumen and the expanded first leg opening, second leg opening and waist opening.

Moreover, the tubular member of the second graft prosthesis is preferably formed of a flexible sheet material rolled into a tubular member of at least one partially overlapping turn, the tubular member being collapsible in diameter under restraint into a collapsed state for advancement through one of the first and second leg openings, the first graft lumen and out the waist opening and self-expandable in diameter upon removal of the restraint to the expanded state, such that the tubular member self-expands until the expanded distal end bears against and is restrained by the trunk vessel wall beyond the area of the aneurysm, defect or injury and the proximal end bears against and is restrained by the attachment seat.

In a second aspect of the invention, the first graft prosthesis is implanted in the collapsed state over a deployment catheter across the bifurcation and the restraint is released to allow the first and second leg opening stents and the waist stent to self-expand and form the first graft lumen. Then, the second graft prosthesis is advanced in its collapsed state over a deployment catheter through the first graft lumen and positioned to extend between the waist opening and patent vessel wall outside the area of the aneurysm, defect or injury.

Then the second graft prosthesis is released and allowed to self-expand to an expanded diameter restrained by the expanded diameter of the waist stent and the blood vessel lumen.

In the third aspect of the invention, the apparatus for repairing or bypassing an aneurysm, defect or injury of the type described includes the two-piece prosthetic graft and the deployment system for deploying the first and second graft prostheses in accordance with the method.

The present invention is particularly advantageously employed to repair or bypass aneurysms involving the abdominal artery at or near the bifurcation of the right and left iliac arteries. However, it may be employed to repair or bypass aneurysms, defects or injuries at bifurcations of other blood vessels.

The ease of insertion into position is enhanced by the single point of percutaneous introduction and advancement allowed by the use of the two separate trunk and limb graft prostheses. The trunk and limb graft prostheses may be selected and sized by the physician to fit the particular patient's anatomy.

The resulting prosthetic graft provides a relatively unobstructed graft lumen with a positive joint relative to the blood flow. This type of joint minimizes the opportunity for leaks and streamlines the flow of blood to reduce the potential for forming clots.

BRIEF DESCRIPTION OF THE DRAWINGS

These and other objects, advantages and features of the invention will become apparent from the following detailed description of the preferred embodiments of the invention, and in which:

FIG. 11 is a perspective view of a first embodiment of an arrangement for restraining the waist stent of the first graft prosthesis when collapsed over the first deployment catheter;

FIG. 12 is a detail view of the release mechanism of the arrangement of FIG. 11 for releasing the waist stent when positioned in the fourth step;

Figure 1:
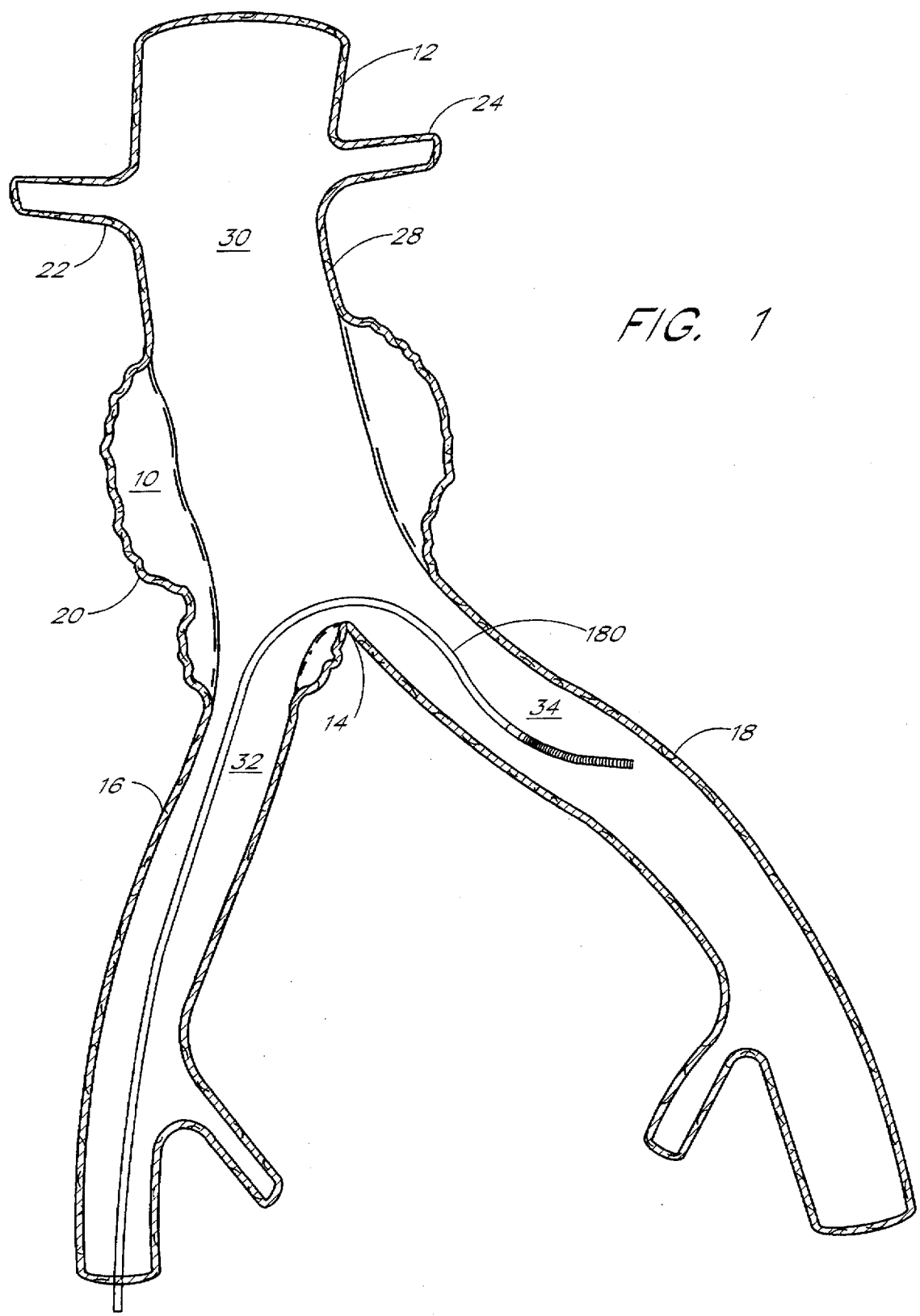
FIG. 1 is a view of an aneurysm of the abdominal aorta at the bifurcation with the right and left iliac arteries and illustrating the first step of the method of the invention wherein a guidewire is advanced from one iliac artery across the bifurcation and into the other iliac artery.

The drawing figures are not necessarily to scale.

DETAILED DESCRIPTION OF THE PREFERRED EMBODIMENTS OF THE INVENTION

The present invention is described in the context of intraluminally bypassing an aneurysm, defect or injury at the bifurcation of the abdominal aorta and the right and left iliac aeries, where the two piece intraluminal graft and method and apparatus for installing it are especially advantageous. It will be understood that the invention has application in intraluminally bypassing aneurysms, defects or injuries formed at other bifurcations of blood vessels in the body, e.g. bifurcations along the carotid and coronary arteries.

Turning to FIG. 1, it depicts an aneurysm (or a defect or other injury) 10 of the abdominal aorta 12 at the bifurcation 14 with the right and left iliac arteries 16, 18 and illustrating the first step of the method of the invention wherein a guidewire 100 is advanced from the right iliac artery 16 across the bifurcation 14 and into the left iliac artery 18, for example. In the typical disease process, the aneurysm 10 expands as the weakened aortic vessel wall 20 stretches under arterial blood pressure in an area of the aortic neck 28 extending generally between the branching of the right and left renal arteries 22, 24 and often inferiorly to include one or both of the iliac arteries 16, 18. The aortic lumen 30 and the iliac artery lumens 32, 34 are therefore expanded in the area affected by the aneurysm 10. The patent vessel wall of the aortic neck 28 superior to the area of the aneurysm 10 retains a healthy diameter of between 20–30 mm, and the aneurysm 10 may double that diameter in the affected area. The unaffected diameters of the right and left iliac artery lumens 32, 34 inferior to the area of the aneurysm 10 are typically between 8–14 mm.

In accordance with a preferred embodiment of the invention, a two piece intraluminal prosthetic graft 100 (shown fully deployed in FIG. 10) for repairing such an abdominal aortic aneurysm 10 is deployed intraluminally to bridge the aneurysm 10 between patent aortic vessel wall in the aortic neck 28 and patent arterial walls of the right and left iliac arteries 16, 18 to seal off aneurysm 10 from blood flow and blood pressure. The prosthetic graft is formed of a first graft prosthesis 110 and a second graft prosthesis 140 which are depicted in the remaining figures in relation to first and second delivery or deployment catheters 160 and 170 and the guidewire 180.

Figure 2:
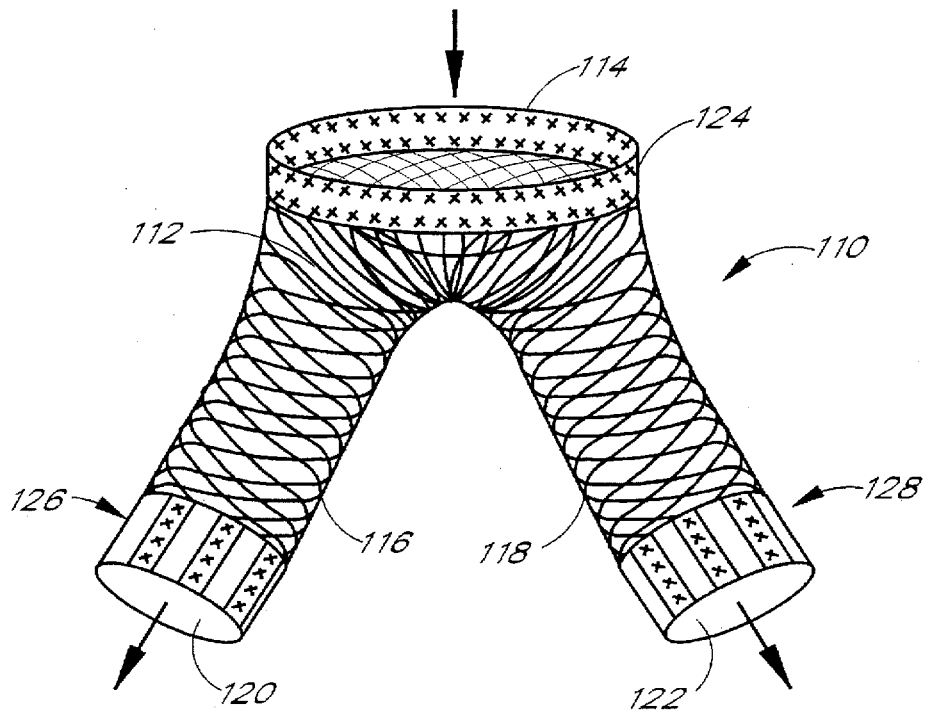
FIG. 2 is a perspective view of a first graft prosthesis in accordance with the invention for bridging the bifurcation of aortic artery and providing an attachment seat for a second graft prosthesis of the invention.

Referring to FIG. 2, the first graft prosthesis 110 has a continuous side wall 112 formed of a woven biocompatible Dacron fabric of a type employed in the above described flexible fabric grafts, e.g. that material disclosed in the above-referenced '473 patent. The first graft prosthesis 110 is formed to resemble trousers without any appreciable seat when expanded to an expanded state in situ having a waist opening 114 and right and left legs 116, 118, terminating in right and left leg openings 120, 122, respectively. The waist opening 114 is formed midway along the length of the continuous side wall 112 between the right and left leg openings 120 and 122. In a collapsed state for percutaneous introduction and advancement through the right or left femoral artery and iliac artery that feeds it, the continuous side wall 112 may be collapsed upon itself in folds, and the waist opening 114 and right and left leg openings 120, 122 closed or contracted.

Preferably, the waist opening 114 is maintained by a waist opening stent 124 for providing a substantially circular attachment seat of a predetermined diameter approximating the diameter of the aortic lumen 30 superior to the area of the aneurysm 10 when it is expanded in the expanded state.

Similarly, the right and left leg openings 120, 122 are preferably maintained by respective right and left leg opening stents 126, 128 that expand until they engage patent side walls of the right and left iliac arteries 16, 18. Preferably the expansion of the leg opening stents 126, 128 applies force outward against the arterial sidewalls that is countered by inward force of the patent arterial side wall. When expanded as described, a first graft lumen 130 extends within the expanded fabric between the expanded waist opening 114 and the right and left leg openings 120, 122 that substantially conforms to the lumens 30, 32 and 34 without substantially stretching the vessel lumen diameters.

The leg opening stents 126 and 128 are preferably formed in ring-shaped bands of plural overlapping turns of sheet material of the type described in the above-referenced '294 and '473 patents incorporated herein by reference. A thin biocompatible metal, e.g. Elgiloy or stainless steel metal foil, having a thickness of about 0.04 mm is preferred to form the ring-shaped bands. The ring-shaped bands may be restrained in a collapsed state to a collapsed diameter about a spool of an deployment catheter and which self-expand in the expanded state to an expanded diameter when the restraint is released. The leg opening stents 126, 128 are preferably attached to the fabric continuous side wall 112 in the manner disclosed in the '473 patent. In this manner, the continuous side wall 112 and leg opening stents 126, 128 are collapsible when restrained in a collapsed state and expandable when unrestrained to an expanded state that conforms with the blood vessel lumens 32, 34 they bear against thereby defining the first graft lumen 130 in the manner taught by the '473 patent.

The waist opening 114 provided by waist opening stent 124 is adapted to be oriented to face superiorly from the aortic bifurcation 14 and toward the aortic lumen 30 of to provide an attachment or restraining seat of predetermined diameter approximating the diameter of the aorta lumen 30 beyond the area of the aneurysm 10 when released from restraint. Therefore, in this case, the waist opening stent 124 is not necessarily subjected to any vessel wall restraint when it is expanded. When it is released from the first deployment catheter 160, the waist opening stent 124 expands within the void of the aneurysm 10 to a maximum free diameter of opening 114. The maximum free diameter of waist opening 114 may be expanded further by force exerted by the expanded distal end of the second graft prosthesis 140. A preferred method of forming, constraining and releasing the waist opening stent 124 is described below with respect to FIGS. 11 and 12.

Figure 3:
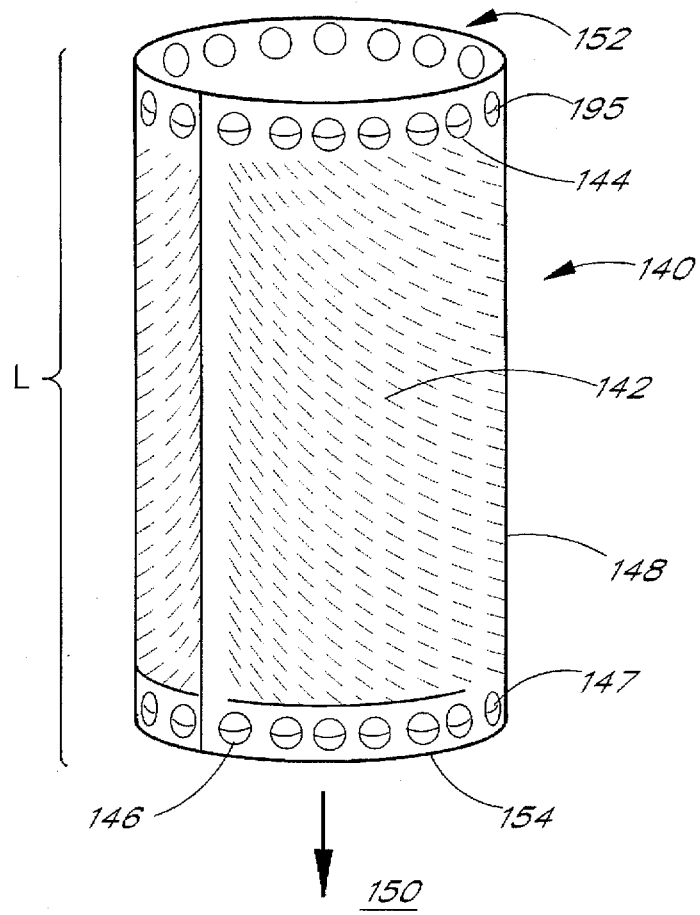
FIG. 3 is a perspective view of the second graft prosthesis in accordance with the invention for engaging the attachment seat of the first prosthesis and the patent aortic side wall for bridging the aneurysm in the aortic artery.
Figure 4:
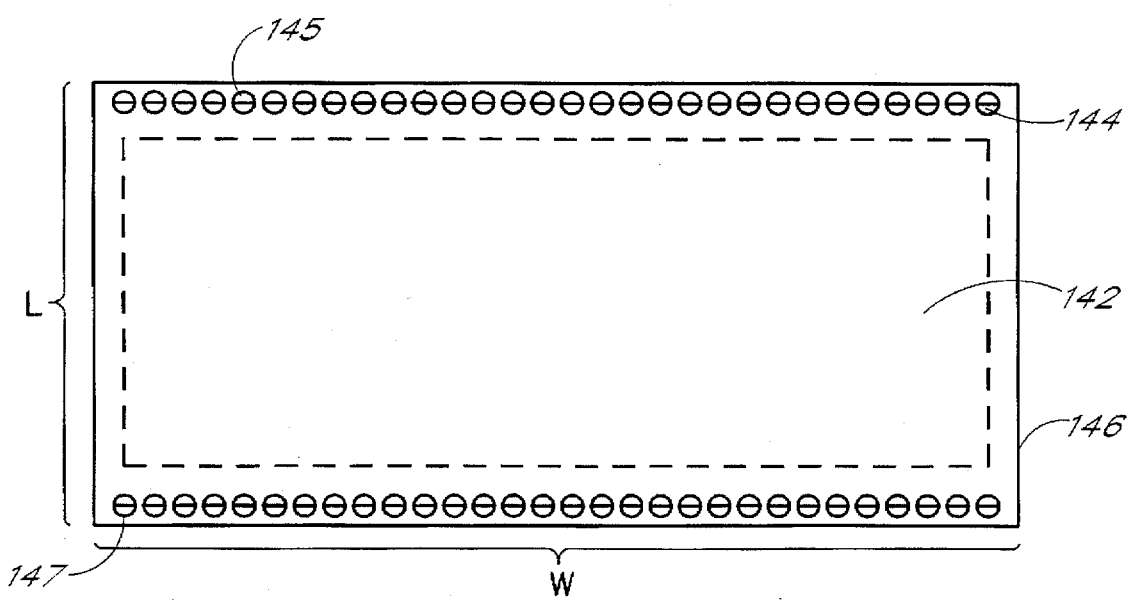
FIG. 4 is a flattened out, plan view of the second graft prosthesis of FIG. 3.
Figure 5:
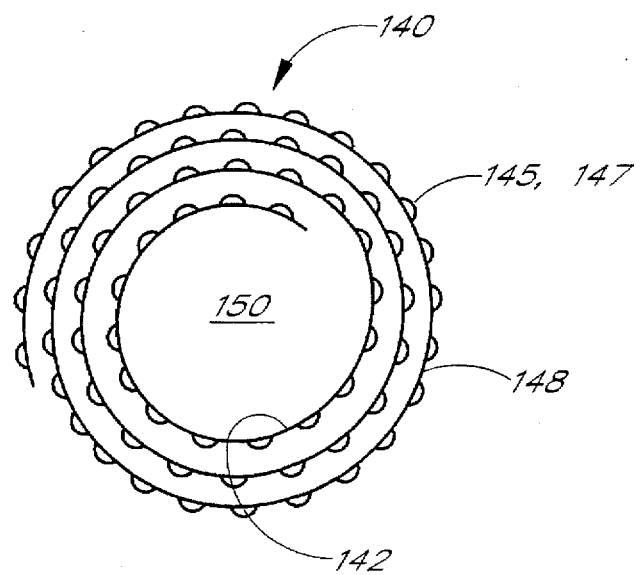
FIG. 5 is an end view of the second graft prosthesis of FIG. 3 when released to form a tubular member of multiple overlapping turns.

The second graft prosthesis 140 is shown in FIG. 3 in an unrestrained side perspective view, in FIG. 4 rolled out in a plan view, and in FIG. 5 in an end view. The second graft prosthesis 140 is preferably formed in a rectangular, flexible, thin sheet 142 having a length L and width W. A thin biocompatible metal, e.g. Elgiloy or stainless steel metal foil, having a thickness of about 0.04 mm is preferred to form the sheet 142, although other materials may be used. The sheet 142 is biased to roll up in its width dimension W into a roll or tubular member 148 of at least one partially overlapping layer or turn, but preferably a number of overlapping turns as shown in FIG. 5, when unrestrained. The tubular member 148 therefore forms a continuous side wall of length L extending between distal and proximal ends and defining a graft lumen 150 extending between distal and proximal ends 152, 154, respectively.

The flexibility of the biocompatible sheet material 142 allows the overall diameter of the tubular member 148 to be collapsed under restraint into a collapsed state and to self-expand upon removal of the restraint to an expanded state. A high expansion ratio of the expanded diameter to the contracted diameter can be attained, and the adjacent turns remain close together in the expanded state to define as great a lumen 150 diameter as possible. In the collapsed state, the reduced diameter allows the second stent prosthesis 140 to be advanced through the femoral artery and iliac artery 16 or 18 and be readily advanced through the leg opening 120 or 122 and waist opening 114 of the previously placed first graft prosthesis 110. During this advancement, the multiple metal foil turns of the tubular member 148 when in the collapsed state are highly visible under fluoroscopy, aiding in attaining the desired position.

As described below, the second graft prosthesis 140 is introduced superior to the aortic bifurcation 14 with the proximal end thereof located within the attachment seat formed by said waist opening stent 124. When unrestrained, the tubular member 148 expands until the expanded distal end bears against and is restrained by the aortic wall beyond the area of the aneurysm 10, and the proximal end bears against and is restrained by the attachment seat to seal the first and second graft lumens with the aorta lumen 30 and the iliac artery lumens 32, 34 and from the aneurysm 10.

The sheet 142 is preferably formed with very small perforations to encourage the growth of neointimal tissue over the surface of the tubular member 148. Rows of larger perforations or circular holes 144 and 146 are arranged along opposite edges of the sheet 142. The circular holes 144 and 146 contain small spring flaps 145 and 147, respectively, in the outer one third of each of the holes. The flaps 145 and 147 protrude slightly outward from the center axis of the second graft prosthesis 140, and the rows of flaps 145, 147 project toward one another. The rows of flaps 145, 147 increase the frictional holding power of the second graft prosthesis 140 in the vessel wall and in the waist band attachment seat until neointimal growth forms through the perforations to secure it to the vessel wall and waist band attachment seat.

In order to introduce and deploy the first and second graft prostheses 110, 140, in accordance with the present invention, first and second introduction and deployment mechanisms for restraining the first and second graft prostheses 110, 140 in the collapsed state are provided. Preferably, the introduction mechanisms are deployment catheters 160 and 170 of the type disclosed in the above-incorporated '294 and '473 patents. In this regard it should be noted that the deployment catheters 160 and 170 preferably have guidewire lumens 162 and 172 so that they may be percutaneously introduced and advanced over a guidewire 180 that has been introduced and advanced to the site. Moreover, deployment catheters 160, 170 may be introduced through introducer catheters (not shown for convenience of illustration except in FIG. 7) that are first introduced over the guidewire 180 to the site or are advanced with the deployment catheters 160, 170 having the first and second graft prostheses 110, 140 collapsed over respective distal portions thereof in the manner shown in the above-incorporated '294 and 473 patents. The outer introducer catheter may act as the restraining mechanism for maintaining the first and second graft prostheses 110, 140 in the collapsed state such that expansion to the expanded state takes place upon retraction of the introducer catheter from the distal portion of the deployment catheter 160, 170 as shown in the above-incorporated '473 patent. Alternatively, or additionally, control cords extending through lumens of the deployment catheters 160, 170 from the proximal ends thereof to the distal portions and terminating in slip knots at distal spool flanges may be employed in the manner described in the above-incorporated '294 patent.

Alternatively, or additionally, looped control cords extending through lumens of the deployment catheters 160, 170 from the proximal ends thereof to the distal portions and terminating in recesses in the deployment catheter and held in place by stainless steel pins which extend through lumens from the distal end of the deployment catheter to the recesses may be employed to secure the stents and graft material in a collapsed state. In this embodiment, the stent is released by pulling the stainless steel pin from the distal end of the delivery catheter thereby releasing the loop in the recess and allowing the stent and graft material to expand to their limits. The looped control cord is withdrawn into the deployment catheter following deployment of the stent. These control cords extend over the collapsed outer turns of the respective stents 124, 126, 128 of the first graft prosthesis 110 or over the outer surface of tubular member 148 of the second graft prostheses surface 148 to maintain the collapsed state until they are pulled on at the proximal ends to untie the slip knots and allow the expansions to the expanded states to take place. For the sake of simplifying the drawings, these details for releasing the restraints on the stents 126, 128 and the tubular member 148 are incorporated from the '294 and '473 patents and not illustrated. One form of a suitable restraint and release mechanism for the waist opening stent 124 is described below in reference to FIGS. 11 and 12.

The method of repairing the abdominal aortic aneurysm 10 close to or involving the aortic bifurcation 14 in accordance with a preferred embodiment of the invention (or any similar aneurysm at other bifurcations of blood vessels) comprises the steps illustrated in FIGS. 1 and 6–10. In general, the first graft prosthesis 110 is advanced to bridge the bifurcation 14 with the left leg 118 extending into the left iliac artery 18 and the right leg 116 extending into the right iliac artery 16 and expanded so that the waist opening 114 is facing the aortic lumen 30 to provide a retention mechanism for receiving the proximal end of the second graft prosthesis 140 when it is expanded distally to it. After the expansion of the first graft prosthesis 110 in situ, the second graft prosthesis 140 is advanced in a collapsed state through the lumen of the first graft prosthesis 110 and positioned in relation to engage with the waist opening 114 when it is expanded to its expanded state. Then, the second graft prosthesis is expanded 140 so that the side wall adjacent the distal end opening engages patent aortic side wall and the proximal end opening expands within the waist opening 114 of the first graft prosthesis and is restrained there from expanding further.

In FIG. 1, the first step of advancing the distal end of the guidewire 180 across the bifurcation 14 is shown. The guidewire 180 has been percutaneously introduced and advanced into the right femoral artery, into the respective right iliac artery coupled thereto, and then across the aortic bifurcation 14 and into the left iliac artery. The direction of introduction is selected by the physician taking asymmetry of the bifurcation 14 and the state of the blood vessels to be traversed into account. As one advantage of the present invention, it is not necessary to approach the bifurcation 14 from cut downs made in both femoral arteries, etc. and with duplicate guidewires, etc. It should be noted that at the sizes of the aortic lumen 30 and the iliac arterial lumens 32, 34 and the length of the aneurysm 10 is mapped out using a contrast agent and fluoroscopic observation, and the physician selects the best sized set from among different sized first and second graft prostheses 110, 140 to bridge the aneurysm 10 when the procedure is completed.

Figure 6:
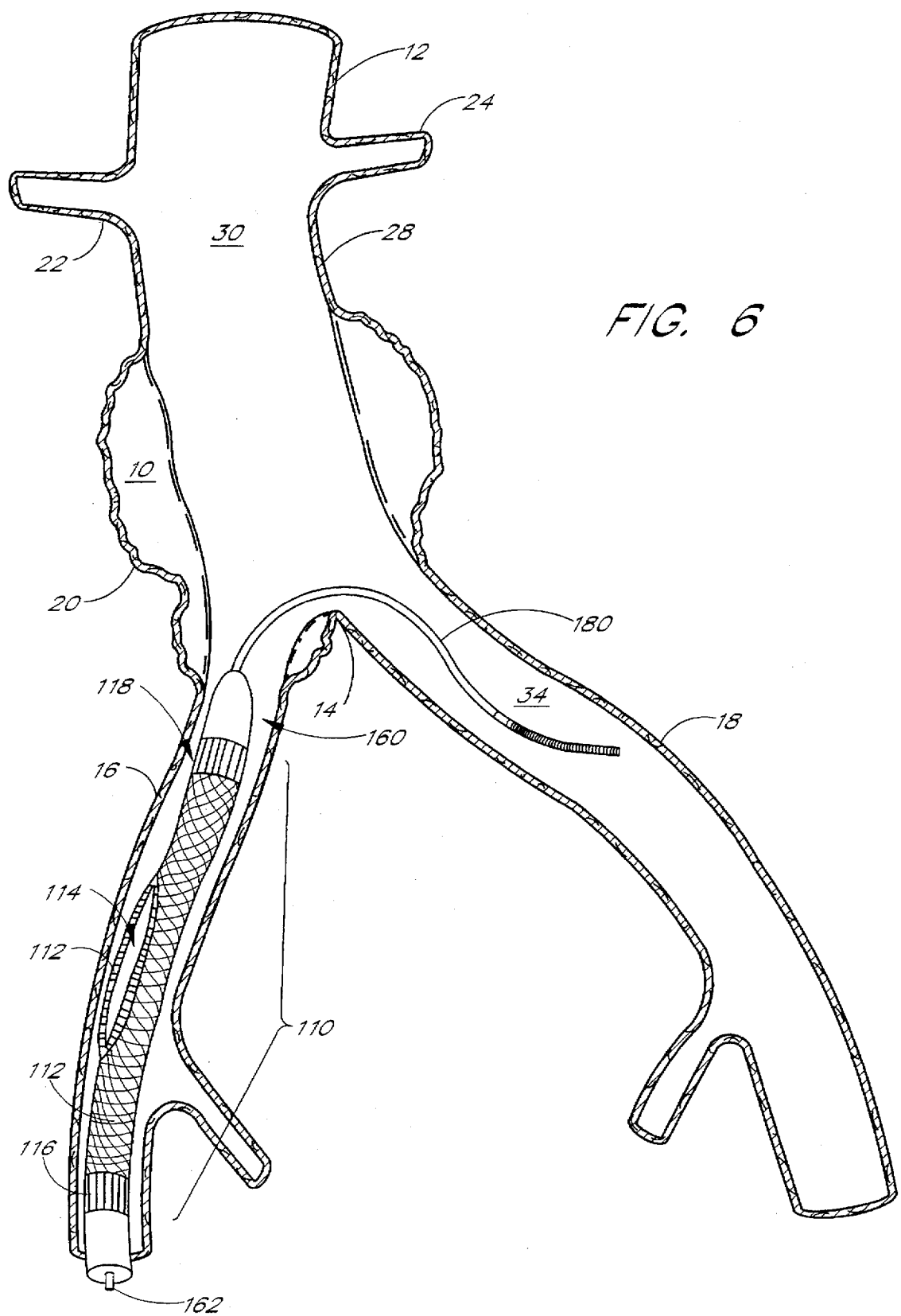
FIG. 6 is a view as in FIG. 1 illustrating the second step of the method of the invention of assembling a first graft prosthesis collapsed about a first deployment catheter and advancing the assembly over the guidewire.

FIG. 6 illustrates the step of assembling the first graft prosthesis 110 collapsed about the distal portion of the first deployment catheter 110. The guidewire lumen 162 in the distal end of the deployment catheter 160 is fired over the guidewire 180, and the assembly is advanced over the guidewire 180 toward the bifurcation 14. In this illustration, the fabric continuous side wall 112 is folded against the distal portion of the first deployment catheter 160 and to extend between the collapsed right leg opening stent 126 and left leg opening stent 128 with the a waist opening stent 124 elongated in a purse opening shape. This collapsed state allows the first graft stent to take on an elongated tubular shape with maximum longitudinal shape and minimal cross-section so that the assembly can be maintained within a diameter of 10–12 French (3.3–4.0 mm). A four fold expansion of the graft lumen diameter in the expanded state to the 8–14 mm diameters of lumens 32 and 34 can be realized.

Figure 7:
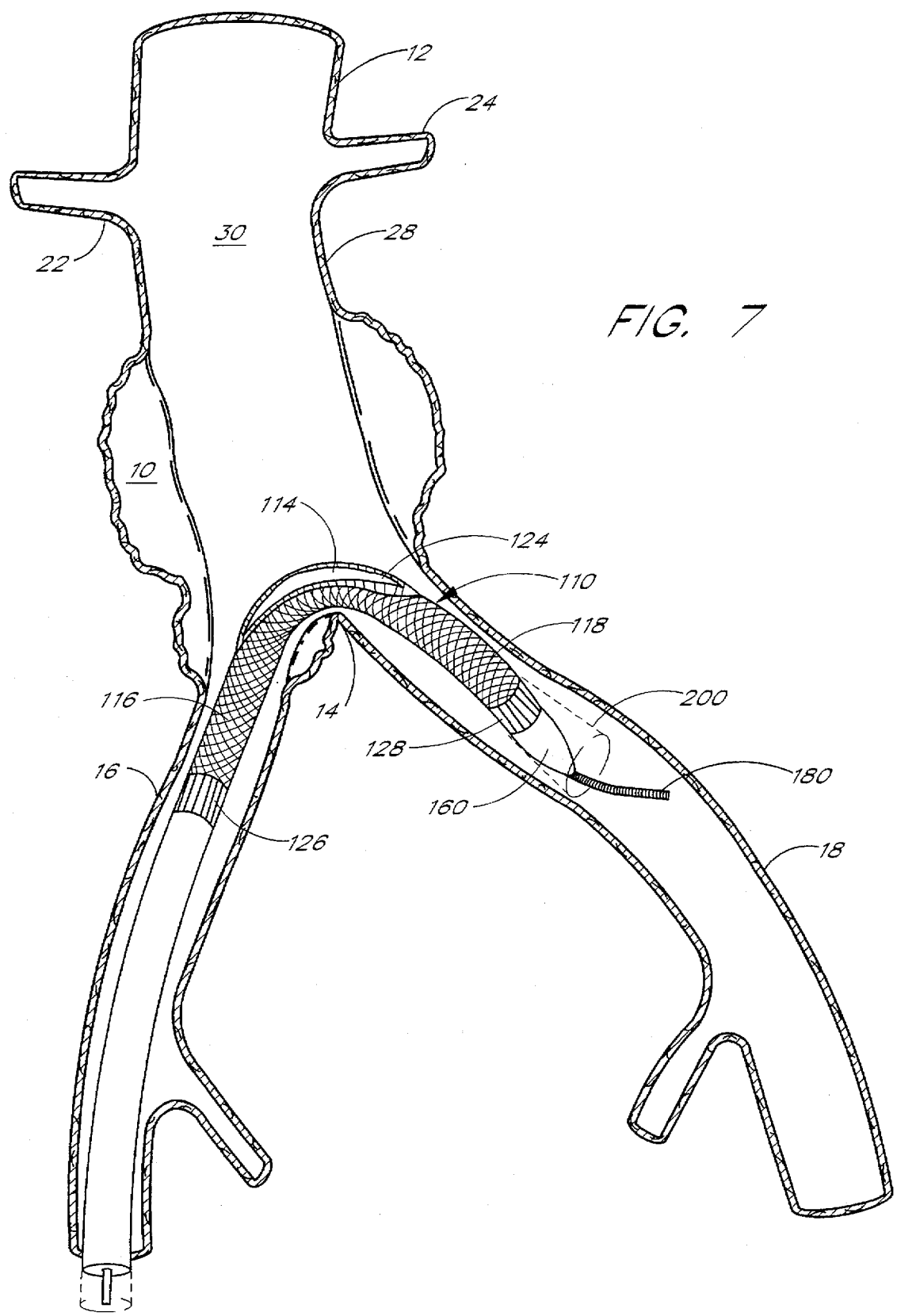
FIG. 7 is a view as in FIG. 1 illustrating the next step of the method of the invention of advancing the assembly of the first graft prosthesis collapsed about a first deployment catheter over the guidewire across the bifurcation and orienting the waist opening toward the lumen of the aorta.

FIG. 7 illustrates the next step of advancing the assembly of the first graft prosthesis 110 collapsed about the first deployment catheter 160 over the guidewire 180 across the bifurcation 14 and orienting the waist opening 114 toward the lumen 30 of the aorta. The right and left leg opening stents 126, 128 are then located in the right and left iliac artery lumens 32, 34. In this view, the introducer catheter 200 is depicted in phantom lines over the first deployment catheter and the first graft prosthesis 110.

Figure 8:
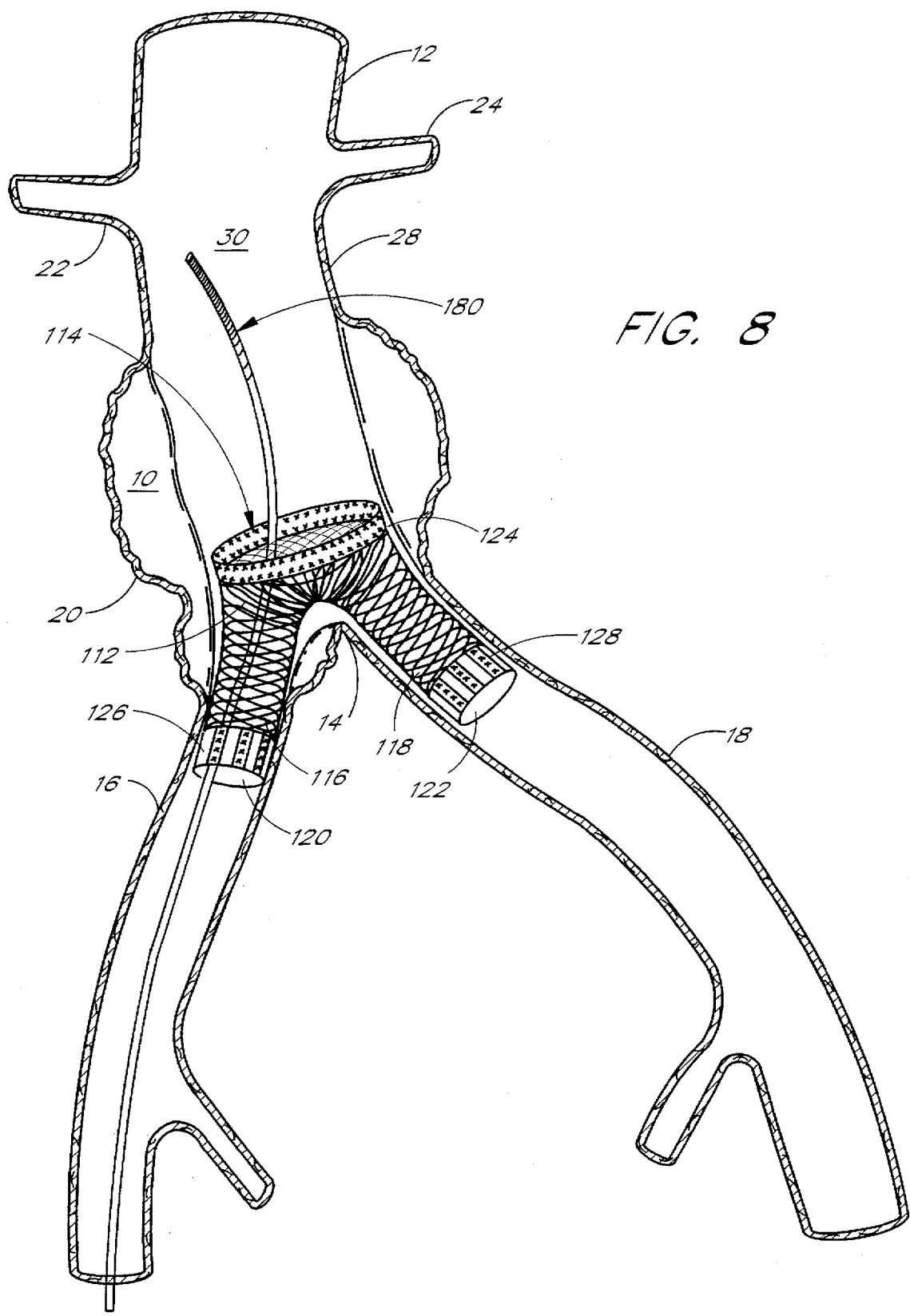
FIG. 8 is a view as in FIG. 1 illustrating the next step of the method of the invention of releasing the self-expanding right and left leg stents and waist stent in the orientation of FIG. 7, retraction of the first deployment catheter, and repositioning of the guidewire.

FIG. 8 illustrates the next step of releasing the self-expanding right and left leg opening stents 126, 128 and waist opening stent 124 in the orientation attained in the step of FIG. 7, resulting in expansion of the continuous side wall 112, and the repositioning of the guidewire 180. Preferably, the left opening stent 128 is first released, then the waist opening stent 124 is released and finally the right opening stent 126 is released. The restraint and release mechanisms for the left and right opening stents are described above. The manner of restraining and releasing the waist opening stent is described in greater detail below.

When released, the right and left leg opening stents 126, 128 bear against arterial walls of the right and left iliac arteries 16, 18 to seal the first graft lumen 130 and iliac artery lumens 32, 34 from the aneurysm 10. The waist opening 114 is oriented to face the aortic lumen 30 to provide an attachment seat of predetermined diameter approximating the diameter of the aortic lumen 30 beyond the area of the aneurysm 10. Generally, the positioning of the right and left legs 116, 118 and the expansion of the waist opening stent 124 to the waist opening diameter for receiving the second graft prosthesis 140 is sufficient to inhibit dislodgement of the first graft prosthesis 110 without the need for any active fixation mechanism. The guidewire 180 is then retracted from the left iliac artery lumen 34 and repositioned to extend distally from the right iliac artery lumen 32 into the aortic lumen 30 beyond the area of the aneurysm 10.

Figure 9:
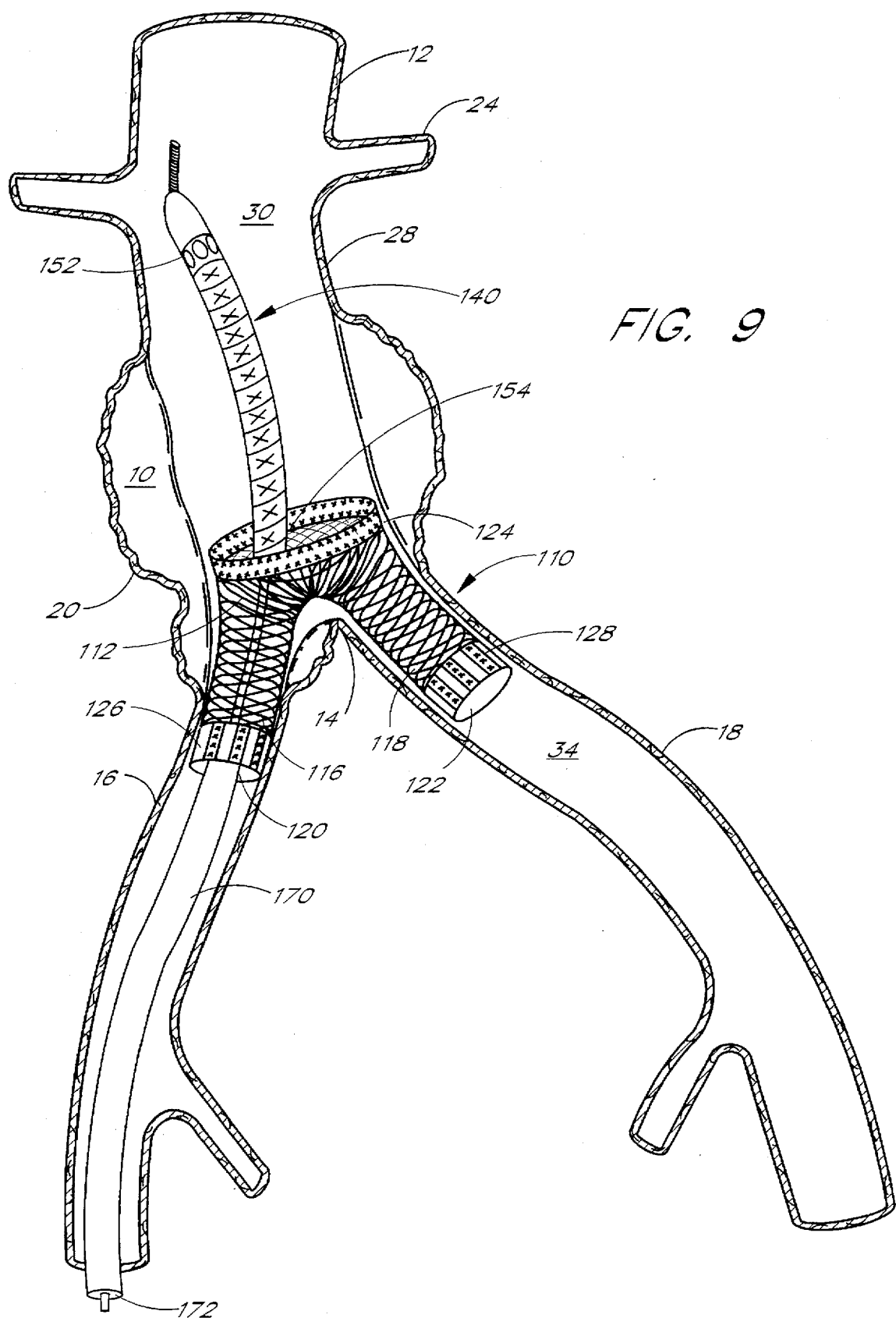
FIG. 9 is a view as in FIG. 1 illustrating the next step of the method of the invention of advancing the assembly of the second graft prosthesis collapsed about a second deployment catheter over the guidewire, through the lumen of the first graft prosthesis and orienting the distal end of the graft prosthesis within the waist opening.

FIG. 9 illustrates the next step of advancing the assembly of the second graft prosthesis 140 collapsed about a second deployment catheter 170 over the guidewire 180, through the right leg opening 120, the lumen of the first graft prosthesis 110, and out of the waist opening 114, to orient the proximal end 154 of the second graft prosthesis 140 within the waist opening 114. The second graft prosthesis 140 is first assembled in a collapsed state about a distal end segment of the second deployment catheter 170 and maintained there by one of the mechanisms described above. The second deployment catheter has a guidewire lumen 172 formed therein that is fired over the guidewire 180 to percutaneously advance the assembly to the depicted position. Because the second graft prosthesis 140 can be rolled up tightly into the tubular member 148 in the collapsed state, over the deployment catheter 170 and within an introducer catheter, the assembly may be advanced easily through the right leg opening 120 and out the waist opening 114. The advancement may be monitored under fluoroscopy because of the radiopacity of the turns of the metal foil 142.

Figure 10:
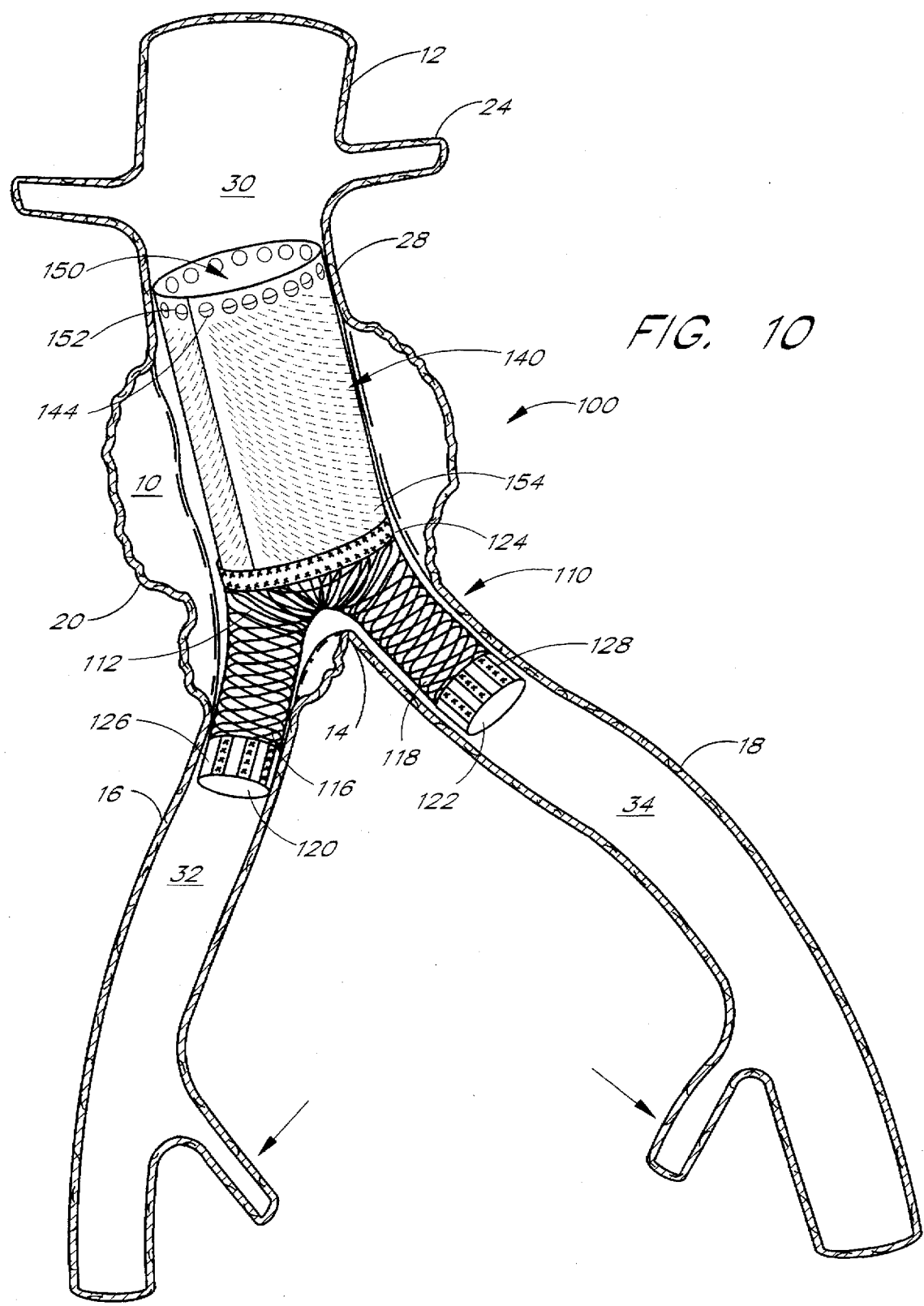
FIG. 10 is a view as in FIG. 9 illustrating the final step of the method of the invention of releasing the self-expanding second graft prosthesis to expand until its distal end is restrained by patent aortic vessel wall superior to the area of the aneurysm and its distal end is restrained within the waist stent of the first graft prosthesis.

FIG. 10 illustrates the final steps of releasing the self-expanding second graft prosthesis to expand until its distal end 152 is restrained by patent aortic vessel wall superior to the area of the aneurysm 10 in the aorta 12 and its distal end is seated and restrained within the waist opening stent 124 of the first graft prosthesis 110. The waist opening stent 124 defines the waist opening 114 maximal diameter and acts as an attachment ring or seat for restraining further expansion of the proximal end 154 of the second graft prosthesis. The second graft prosthesis 140 expands so that the continuous side wall 148 adjacent the expanded distal end 152 bears against the aortic arterial wall beyond the area of the aneurysm 10, and the continuous side wall 148 adjacent to the expanded proximal end 154 bears against the attachment seat to seal the second graft lumen 150 and the aortic lumen 30 from the aneurysm 10. The rows of flaps 145, 147 increase the frictional holding power of the second graft prosthesis 140 against the vessel wall and in the waist band attachment seat. The waist opening 114 and lumen of the first graft prosthesis 110 are thereby pressure sealed from the aneurysm 10. The higher blood pressure within the lumen 150 and the growth of neointimal tissue also helps maintain the seal.

During the placement, as the tubular member 148 expands, it exhibits considerable stiffness and no foreshortening thereby reducing the chance of incorrect placement due to the influence of blood pressure or changes in length as can occur with other self-expanding fabric, foil and wire stents introduced into this site.

Thereafter, the second deployment catheter 170 and the guidewire 180 (and any introducer catheter) are withdrawn, completing the procedure for positioning the two piece intraluminal graft prosthesis of the invention. The self expansion of the second graft prosthesis 140 simplifies the withdrawal of these components from the graft lumen 150 and the smaller leg lumen and leg opening 120.

Turning to FIG. 11, it is a perspective view of a first arrangement for restraining the waist opening stent 124 in an elongated manner when the first graft prosthesis 110 is collapsed over the first deployment catheter 160. FIG. 12 is a detail view of the release mechanism of the first arrangement of FIG. 11 for releasing the waist opening stent 124 when positioned in the fourth step of FIG. 7.

In FIG. 11, the waist opening stent 124 is formed of a single wire coil spring that is flexible enough to be compressed or collapsed into an elongated oval and restrained by a suture or thread 182. The thread 182 is wrapped around the collapsed coil spring and the outer surface of the fabric continuous side wall 112 in double strands and looped over the end 184 of an elongated release pin 186 extending down a lumen of the first deployment catheter 160. The waist opening stent 124 formed of the closely wound coil spring is enclosed in a draw string type loop or channel created in the graft material at the waist opening border. As shown in FIG. 12, the release pin distal end 184 is accessible through a recess 190 in the release pin lumen 192 of the first deployment catheter 160, and the end loop 188 of the thread 182 is fitted over it. The double strands of the thread 182 extend proximally through a further lumen (or the guide wire lumen) of deployment catheter 160 and out the proximal end thereof.

Figure 13:
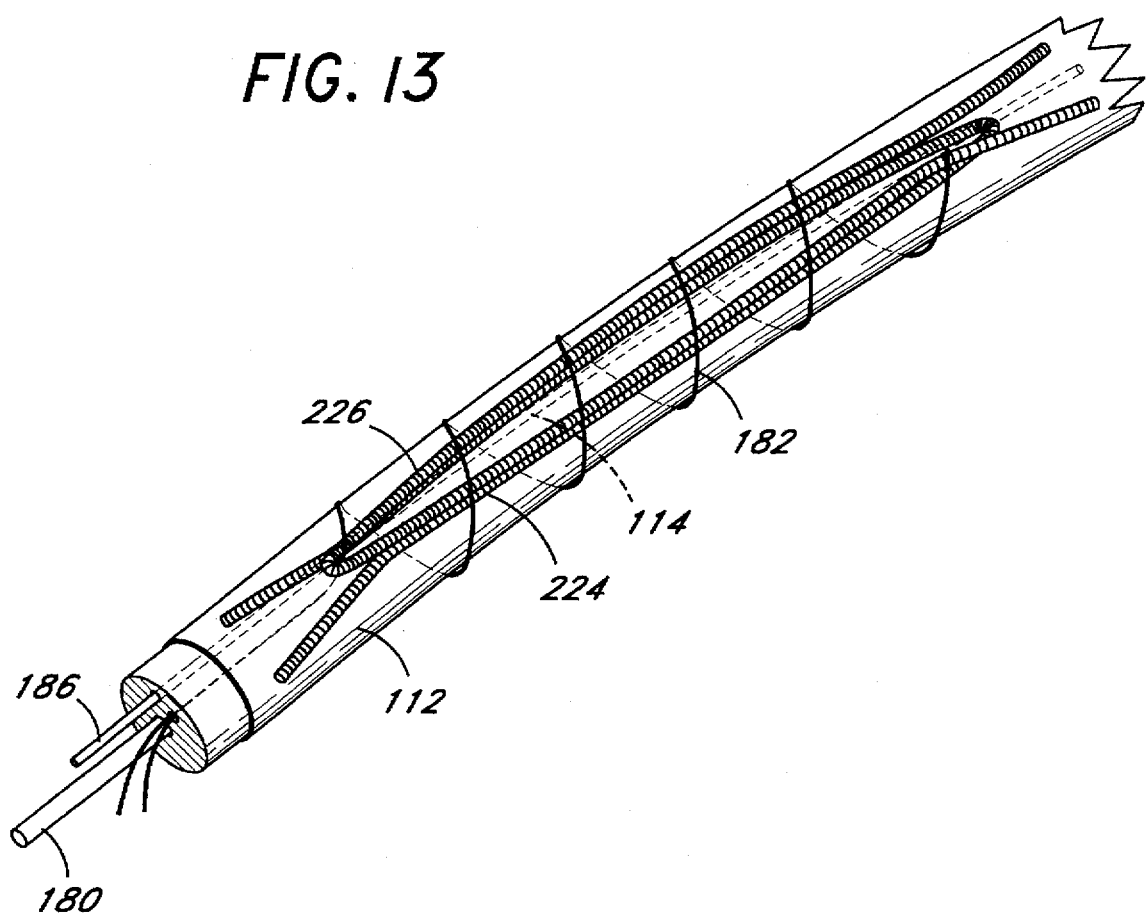
FIG. 13 is a perspective view of a first embodiment of an arrangement for restraining the waist stent of the first graft prosthesis when collapsed over the first deployment catheter.
Figure 14:
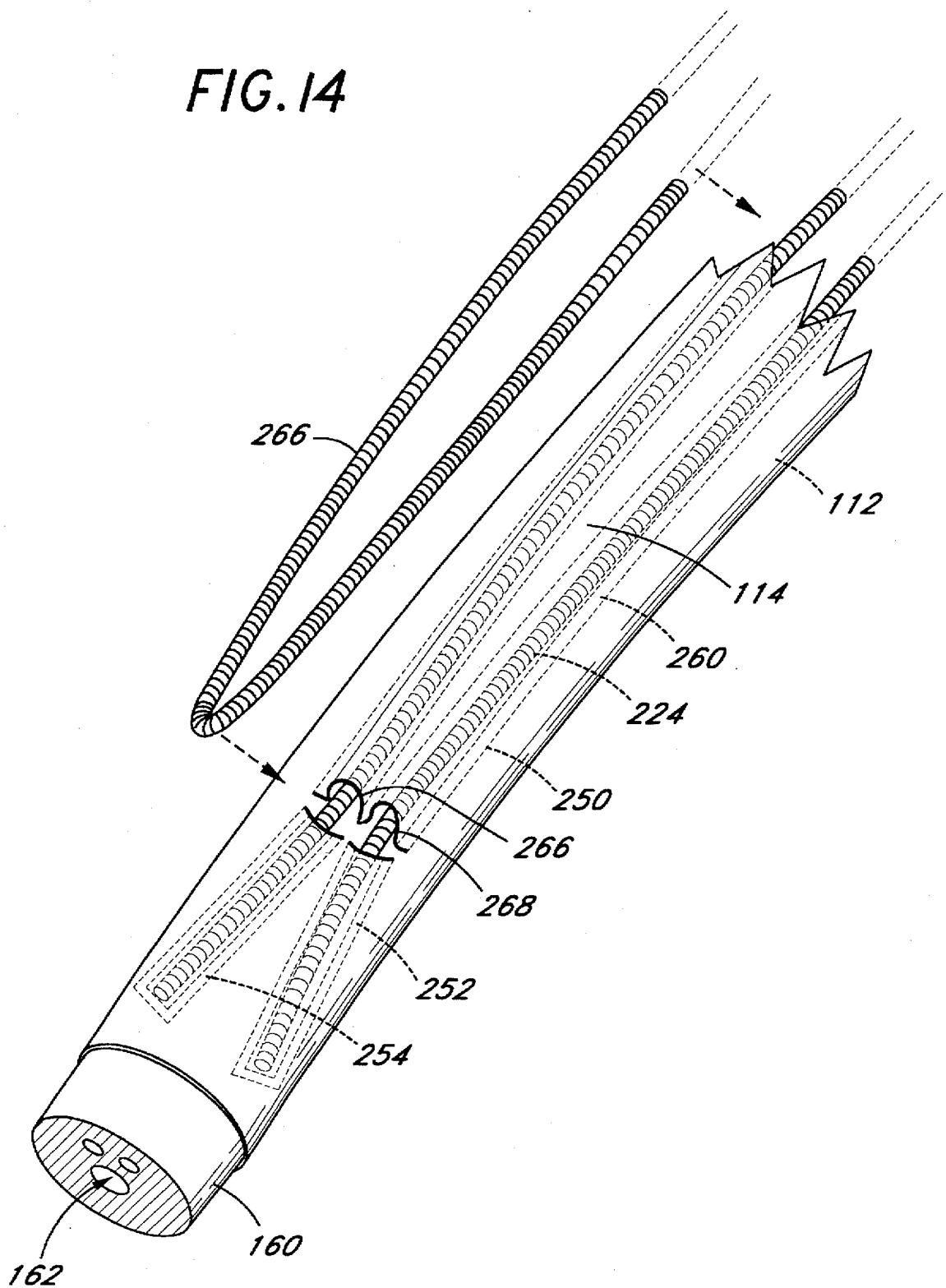
FIG. 14 is a exploded, detail of the perspective view of FIG. 13.

Turning to FIGS. 13 and 14, they show an alternative arrangement for creating the waist opening stent 124 surrounding the waist opening 114 and the manner of restraining the stent 124 in an elongated manner when the first graft prosthesis 110 is collapsed over the first deployment catheter 160. In this arrangement, the waist opening stent 124 is preferably formed of two lengths of straight, closely wound coil springs 224 and 226 that extend in overlapping manner alongside one another and are folded about their mid-points. As shown in the detail view of FIG. 14, a first fabric loop or channel 250 is formed in the fabric continuous side wall 112 and extends around the waist opening 114 to receive the coil spring 224. As also shown in FIG. 14, the ends of coil spring 224 are secured in end pockets 252 and 254 of the first channel 250 extending away from one end of the elongated waist opening 114 formed in the fabric continuous side wall 112. A second fabric loop or channel 260 is formed to extend in parallel with the first channel 250 and terminate in a further pair of end pockets (not shown) extending away from the opposite end of the elongated waist opening 114 as shown in FIG. 13. The mid points of each coil spring 224, 226 are exposed at channel end openings, e.g. channel end openings 266 and 268 of the second channel 260 depicted in FIG. 14.

In assembly, the ends of the first and second coils 224, 226 are slipped into the respective channel end openings and extended through channels 250, 260 until the coil ends are fitted into the end pockets for each channel.

The resulting configuration is similar to two partially overlapping horseshoes in which the apex of each shoe opposes the other and lies over the leg ends of the other shoe. When released from the collapsed position shown in FIG. 13, the two coil springs 224, 226 assume overlapping circular shapes and draw their respective free ends toward one another, thereby forming the circular seat in the waist opening 114.

In use, after the assembly of the collapsed first graft prosthesis 110 over the first deployment catheter 160 is positioned as shown in FIG. 7 and the introducer catheter 200 is withdrawn, the release pin 186 is retracted proximally so that the release pin distal end 186 releases the end loop 188. The coil spring or springs 224, 226 forming the waist opening stent 124 then spring into the circular configuration providing the seat for the second graft prosthesis 140. The looped restraining thread 182 is then drawn out through the lumen in the first deployment catheter 160.

This method may be employed at other bifurcated vessel sites in the body where aneurysms occur. Different sized first and second graft prostheses 110, 140 and related deployment catheters may be necessary for specific sites, although the high ratio of expansion may suffice for a wide range of vessel lumens.

Although the above described method preferably employs the self-expanding second graft prosthesis 140 and the self-expanding stents 124, 126, 128 of the first graft prosthesis, it will be understood that the method may be employed to position a first graft prosthesis having leg opening stents, for example, that are not self-expanding and are expanded by the deployment catheter and/or employ active fixation mechanisms. However, if a balloon expandable, tubular trunk graft were used instead, the deflated balloon would be more difficult to withdraw through the first and second graft prostheses lumens and could catch and dislodge the tubular member 148 or tear, leaving a fragment that could and create an embolism. Consequently, the above-described embodiments are preferred for this reason and for other reasons of size and convenience of installation.

Moreover, although the described method employs deployment catheters optionally with introducer catheters and restraining mechanisms for placing the first and second graft prostheses in the collapsed state and release mechanisms for allowing the self-expansion thereof of the type described in the above-incorporated '294 and '473 patents, other mechanisms may be employed to perform these functions. For example, simpler introducer catheters may be employed with the collapsed first and second prostheses simply collapsed within the introducer catheter lumens and then expelled from the lumens by a pusher mechanism.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. A two piece prosthetic graft for intraluminally bypassing an aneurysm, defect or injury in a vessel wall close to or involving a bifurcation of a trunk vessel having a trunk vessel wall and lumen into first and second branch vessels having first and second branch vessel walls and lumens, said graft comprising:

a first graft prosthesis having a continuous side wall extending a length between a first leg opening stent adapted to be expanded into contact with the first branch vessel wall and to define a first leg opening and a second leg opening stent adapted to be expanded into contact with the second branch vessel wall and to define a second leg opening, means for defining a waist opening formed in said fabric side wall along the length of said first graft prosthesis, the continuous side wall and first and second leg opening stents being expandable to an expanded state bridging the bifurcation with said waist opening adapted to be oriented to face away from the bifurcation and toward the lumen of the trunk vessel to provide an attachment seat of predetermined size and defining a first graft lumen extending between said expanded waist lumen and said expanded first leg opening in the first branch vessel lumen and said second leg opening in the second branch vessel lumen; and a second graft prosthesis formed of tubular member having a length and a continuous side wall between distal and proximal ends and defining a second graft lumen extending between distal and proximal leg openings, respectively, the tubular member having a collapsed state for advancement of said proximal end into alignment with respect to said waist opening and bridging said aneurysm, defect or injury and being expandable in size to an expanded state with said proximal end thereof expanded into engagement with said attachment seat and the distal end thereof bearing against and restrained by the trunk vessel wall beyond the area of the aneurysm to seal the first and second graft lumens with the trunk vessel lumen and from the aneurysm.

2. The two piece prosthetic graft of claim 1 wherein:

said continuous side wall and said first and second leg opening stents of said first prosthetic graft are collapsible when restrained in a collapsed state and expandable when unrestrained to an expanded state defining said first graft lumen and said expanded first leg opening, second leg opening and waist opening.

3. The two piece prosthetic graft of claim 2 wherein:

said tubular member of said second graft prosthesis is formed of a flexible sheet material rolled into a roll of at least one partially overlapping turn and is collapsible in size under restraint into a collapsed state for advancement through one of said first and second leg openings, said first graft lumen and out said waist opening and self-expandable in size upon removal of the restraint to said expanded state, such that the tubular member self-expands until the expanded distal end bears against and is restrained by the trunk vessel wall beyond the area of the aneurysm, defect or injury and the proximal end bears against and is restrained by said attachment seat.

4. The two piece prosthetic graft of claim 3 wherein:

said tubular member is formed of a flexible sheet material rolled into a plurality of complete overlapping turns in said collapsed state.

5. The two piece prosthetic graft of claim 4 wherein:

said tubular member is formed of a flexible sheet material that is radiopaque.

6. The two piece prosthetic graft of claim 1 wherein:

said tubular member of said second graft prosthesis is formed of a flexible sheet material rolled into a roll of at least one partially overlapping turn and is collapsible in size under restraint into a collapsed state for advancement through one of said first and second leg openings, said first graft lumen and out said waist opening and self-expandable in size upon removal of the restraint to said expanded state, such that the tubular member self-expands until the expanded distal end bears against and is restrained by the trunk vessel wall beyond the area of the aneurysm, defect or injury and the proximal end bears against and is restrained by said attachment seat.

7. The two piece prosthetic graft of claim 6 wherein:

said tubular member is formed of a flexible sheet material rolled into a plurality of complete overlapping turns in said collapsed state.

8. The two piece prosthetic graft of claim 7 wherein:

said tubular member is formed of a flexible sheet material that is radiopaque.

9. The two piece prosthetic graft of claim 1 wherein:

said waist opening stent is formed of resilient material adapted to be restrained for introduction and to form a band-shaped seat for defining said waist opening when unrestrained.

10. The two piece prosthetic graft of claim 1 wherein:

said first and second leg opening stents are formed of strips of resilient material rolled up into ring-shaped bands that may be restrained in a collapsed state to a collapsed size and which self-expand in said expanded state to an expanded size when the restraint is released.

11. A two piece prosthetic graft for repairing an abdominal aortic aneurysm in the arterial wall close to or involving the aortic bifurcation comprising the abdominal aorta and the right and left iliac arteries, said graft comprising:

a first graft prosthesis having a continuous, fabric side wall extending between a self-expanding right leg opening stent and a self-expanding left leg opening stent and having a self-expanding waist stent in the continuous side wall thereof between the right and left leg opening stents, the continuous side wall and opening stents being collapsible when restrained in a collapsed state and expandable when unrestrained to an expanded state defining a first graft lumen extending between a waist opening, a right leg opening, and a left leg opening, said right and left opening stents adapted to be located and released from restraint in the right and left iliac arteries outside the area affected by the aneurysm to bear against the right and left iliac artery walls to seal the first graft lumen and iliac arteries from the aneurysm, and said waist opening adapted to be oriented to face superiorly from the aortic bifurcation and toward the lumen of the aorta to provide an attachment seat of predetermined size approximating the diameter of the aorta lumen beyond the area of the aneurysm when said waist opening stent is expanded; and a second graft prosthesis formed of a flexible sheet material rolled to form a tubular member of at least one partially overlapping turn having a length and a continuous side wall between distal and proximal ends and defining a graft lumen within the tubular member extending between distal and proximal end openings, respectively, the turns of the tubular member being collapsible under restraint into a collapsed state and expandable upon removal of the restraint to an expanded state when introduced superior to the aortic bifurcation with the proximal end thereof located within said attachment seat formed by said waist opening stent such that the tubular member expands until the expanded distal end bears against and is restrained by the aortic arterial wall beyond the area of the aneurysm and the proximal end bears against and is restrained by said attachment seat to seal the first and second graft lumens with the aorta lumen and from the aneurysm.

12. The two piece prosthetic graft of claim 11 wherein:

said tubular member is formed of a flexible sheet material rolled into a plurality of complete overlapping turns in said collapsed state.

13. The two piece prosthetic graft of claim 12 wherein:

said tubular member is formed of a flexible sheet material that is radiopaque.

14. The two piece prosthetic graft of claim 11 wherein:

said first and second leg opening stents are formed of strips of resilient material rolled up into ring-shaped bands that may be restrained in a collapsed state to a collapsed size and which self-expand in said expanded state to an expanded size when the restraint is released.

15. The two piece prosthetic graft of claim 11 wherein:

said waist opening stent is formed of resilient material adapted to be restrained for introduction and to form a band-shaped seat for defining said waist opening when unrestrained.

16. A method of bypassing an aneurysm, defect or injury in a trunk blood vessel wall close to or involving a bifurcation of the trunk blood vessel into first and second branch vessels having first and second branch vessel walls and lumens comprising the steps of:

percutaneously introducing and advancing a first elongated graft prosthesis in a collapsed state into a position bridging the bifurcation, the first graft prosthesis having a continuous side wall extending between a first leg opening stent and a second leg opening stent and having a waist opening stent in the continuous side wall thereof between the first and second leg opening stents defining a waist opening when expanded, the continuous side wall and leg and waist opening stents being collapsible in the collapsed state during advancement and expandable to an expanded state to define a first graft lumen extending between the waist opening and the first and second leg openings;

expanding the first leg opening stent, the second leg opening stent and the continuous side wall with the waist opening stent oriented to the trunk vessel lumen so that the first and second leg opening stents bear against first and second branch vessel walls to seal the first graft lumen from the aneurysm, defect or injury;

expanding the waist opening stent oriented to face the trunk vessel lumen to a fixed waist opening size to provide an attachment seat of predetermined size;

advancing a second graft prosthesis, having a continuous side wall extending between distal and proximal end openings thereof, the continuous side wall being collapsible in the collapsed state expandable to an expanded state to define an expanded continuous side wall of a second graft lumen, in said collapsed state to align said proximal end opening within said waist opening; and expanding the second graft prosthesis so that the continuous side wall adjacent the expanded distal end opening bears against the trunk vessel wall beyond the area of the aneurysm, defect or injury and the continuous side wall adjacent to the proximal end opening bears against said attachment seat to seal the second graft lumen and trunk vessel from the aneurysm, defect or injury and to seal the waist opening of the first graft lumen.

17. A method of repairing an abdominal aortic aneurysm in the arterial wall close to or involving the aortic bifurcation comprising the aorta and the right and left iliac arteries comprising the steps of:

percutaneously introducing and advancing a guidewire into one of the right and left femoral arteries, into the respective one of the right and left iliac arteries coupled thereto and then across the aortic bifurcation and into the other one of the right and left iliac arteries;

assembling a first elongated graft prosthesis in a collapsed state about a distal end segment of a first deployment catheter, the first graft prosthesis having a continuous side wall extending between a right leg opening stent and a left leg opening stent and having a waist opening stent in the continuous side wall thereof between the right and left leg openings, the continuous side wall and opening stents being collapsible in the collapsed state against the first deployment catheter distal end segment during introduction and expandable to an expanded state to define an expanded continuous side wall defining a first graft lumen extending between a respective right leg opening, left leg opening and waist opening, the first deployment catheter having a guidewire lumen formed therein adapted to be fitted over the guidewire;

fitting the guidewire lumen over the guidewire and introducing the assembly of the first deployment catheter and the collapsed first graft prosthesis over the guidewire across the aortic bifurcation to locate the right and left leg opening stents in the right and left iliac arteries with the waist opening and stent oriented to face the lumen of the aorta;

expanding the right opening stent, the left opening stent and the continuous side wall with the waist opening stent oriented to the lumen of the aorta so that the right and left stents bear against arterial walls of the right and left iliac arteries to seal the first graft lumen and iliac arteries from the aneurysm;

expanding the waist opening oriented to face the lumen of the aorta to provide an attachment seat of predetermined size approximating the diameter of the aorta lumen beyond the area of the aneurysm;

withdrawing the first deployment catheter;

repositioning the guidewire to extend from the one of the right and left iliac arteries into the lumen of the aorta beyond the area of the aneurysm;

assembling a second graft prosthesis in a collapsed state about a distal end segment of a second deployment catheter, the second graft prosthesis having a continuous side wall extending between distal and proximal end openings thereof, the continuous side wall being collapsible in the collapsed state against the second deployment catheter distal end segment during introduction and expandable to an expanded state to define an expanded continuous side wall of a second graft lumen, the second deployment catheter having a guidewire lumen formed therein adapted to be fitted over said guidewire;

fitting the second deployment catheter guidewire lumen over the guidewire and introducing the assembly of the second deployment catheter and the collapsed second graft prosthesis over the guidewire past the aortic bifurcation to locate the distal end opening adjacent the aortic arterial wall beyond the area of the aneurysm and the proximal end opening within said attachment seat formed by said waist opening stent;

expanding the second graft prosthesis so that the continuous side wall adjacent the expanded distal end opening bears against the aortic arterial wall beyond the area of the aneurysm and the continuous side wall adjacent to the proximal end opening bears against said attachment seat to seal the second graft lumen and aorta from the aneurysm and to seal the waist opening of the first graft lumen and to release the second graft prosthesis from the second deployment catheter; and percutaneously withdrawing the second deployment catheter and guide wire.

18. A method of repairing an aneurysm, defect or injury in a trunk blood vessel wall close to or involving a bifurcation of the trunk blood vessel into first and second branch blood vessels having branch blood vessel lumens and vessel walls comprising the steps of:

percutaneously introducing and advancing a guidewire into one of the first and second blood vessel lumens and across the bifurcation and into the other one of the first and second blood vessels;

assembling a first elongated graft prosthesis in a collapsed state about a distal end segment of a first deployment catheter, the first graft prosthesis having a continuous side wall extending between a first leg opening stent and a second leg opening stent and having a waist opening stent in the continuous side wall thereof between the first and second leg openings, the continuous side wall and opening stents being collapsible in the collapsed state against the first deployment catheter distal end segment during introduction and expandable to an expanded state to define an expanded continuous side wall defining a first graft lumen extending between a respective first leg opening, second leg opening and waist opening, the first deployment catheter having a guidewire lumen formed therein adapted to be fitted over the guidewire;

fitting the first deployment catheter guidewire lumen over the guidewire and introducing the assembly of the first deployment catheter and the collapsed first graft prosthesis over the guidewire across the trunk vessel bifurcation to locate the first and second leg opening stents in the first and second blood vessel lumens with the waist opening and stent oriented to face the trunk vessel lumen;

expanding the first leg opening stent, the second leg opening stent and the continuous side wall with the waist opening stent oriented to the lumen of the aorta so that the first and second leg opening stents bear against the first and second branch vessel walls to seal the first graft lumen and branch vessels from the aneurysm, defect or injury;

expanding the waist opening stent oriented to face the lumen of the aorta to provide an attachment seat of predetermined size approximating the diameter of the trunk vessel lumen beyond the area of the aneurysm, defect or injury;

withdrawing the first deployment catheter;

repositioning the guidewire to extend into the trunk vessel lumen extending across the area of the aneurysm, defect or injury;

assembling a second graft prosthesis in a collapsed state about a distal end segment of a second deployment catheter, the second graft prosthesis having a continuous side wall extending between distal and proximal end openings thereof, the continuous side wall being collapsible in the collapsed state against the second deployment catheter distal end segment during introduction and expandable to an expanded state to define an expanded continuous side wall of a second graft lumen, the second deployment catheter having a guidewire lumen formed therein adapted to be fitted over said guidewire;

fitting the second deployment catheter lumen over the guidewire and introducing the assembly of the second deployment catheter and the collapsed second graft prosthesis over the guidewire past the bifurcation to locate the distal end opening adjacent the trunk vessel wall beyond the area of the aneurysm, defect or injury and the proximal end opening within said attachment seat formed by said waist opening stent;

expanding the second graft prosthesis so that the continuous side wall adjacent the expanded distal end opening bears against the trunk vessel wall beyond the area of the aneurysm, defect or injury and the continuous side wall adjacent to the proximal end opening bears against said attachment seat to seal the second graft lumen and trunk vessel from the aneurysm, defect or injury and to seal the waist opening of the first graft lumen and the second graft prosthesis and to release said second graft prosthesis from said second deployment catheter; and percutaneously withdrawing the second deployment catheter and guide wire.

19. A two piece prosthetic graft for repairing an aneurysm, defect or injury in a blood vessel wall close to or involving a bifurcation of a trunk blood vessel and first and second branch blood vessels having branch blood vessel lumens and walls and an introduction and deployment system for said two piece prosthetic graft, said graft comprising:

a first graft prosthesis having a continuous, side wall extending between a right leg, expandable opening stent and a left leg, expandable opening stent and having a waist, expandable stent in the continuous side wall thereof between the right and left leg openings, the expandable opening stents being collapsible when restrained in a collapsed state and expandable when unrestrained to an expanded state defining a first graft lumen extending between expanded right leg, left leg, and waist openings; and a second graft prosthesis formed of a flexible sheet material rolled into a tubular member of at least one partially overlapping turn and defining a graft lumen extending between distal and proximal end openings formed by the tubular member when in an expanded shape, the continuous side wall being collapsible into a collapsed state and expandable to an expanded state; and said introduction and deployment system comprising:

first introduction and deployment means for introducing said first graft prosthesis in said collapsed state across the bifurcation to locate the right and left leg opening stents in the first and second branch blood vessels to bridge the area affected by the aneurysm, defect or injury and for deploying the right leg opening stent, the left leg opening stent and the continuous side wall such that the right and left stents bear against the first and second branch blood vessel walls to seal the first graft lumen and the branch blood vessels from the aneurysm, defect or injury, and for deploying the waist opening stent to face the trunk blood vessel lumen to provide an attachment seat of predetermined size approximating the diameter of the trunk blood vessel lumen beyond the area of the aneurysm, defect or injury; and second introduction and deployment means for introducing said second graft prosthesis in the collapsed state to locate the distal end opening adjacent the trunk blood vessel wall beyond the area of the aneurysm, defect or injury and the proximal end opening within said attachment seat formed by said waist opening stent and for deploying the second graft prosthesis so that the tubular member expands until the expanded distal end bears against and is restrained by the trunk blood vessel wall beyond the area of the aneurysm, defect or injury and the proximal end bears against and is restrained by said attachment seat to seal the first and second graft lumens with the blood vessel lumens and from the aneurysm, defect or injury.

20. The system of claim 19 wherein said first introduction and deployment means further comprises:

a first deployment catheter having a distal end segment, means for maintaining said first graft prosthesis in said collapsed state along said distal end segment during introduction and for releasing said first graft prosthesis, means for restraining said waist opening stent in a collapsed position and for releasing said waist opening stent to assume said expanded state, and a guidewire lumen formed therein adapted to be fitted over the guidewire for allowing introduction of the assembly of the first deployment catheter and the collapsed first graft prosthesis across the bifurcation.

21. The system of claim 19 wherein:

said tubular member is formed of a flexible sheet material rolled into a plurality of complete overlapping turns in said collapsed state.

22. The system of claim 21 wherein:

said tubular member is formed of a flexible sheet material that is radiopaque.

23. The system of claim 21 wherein:

said first and second leg opening stents are formed of strips of resilient material rolled up into ring-shaped bands that may be restrained in a collapsed state to a collapsed size and which self-expand in said expanded state to an expanded size when the restraint is released.

24. The system of claim 19 wherein:

said first and second leg opening stents are formed of strips of resilient material rolled up into ring-shaped bands that may be restrained in a collapsed state to a collapsed size and which self-expand in said expanded state to an expanded size when the restraint is released.

25. The system of claim 24 wherein:

said waist opening stent is formed of a resilient, ring-shaped coil spring attached to said continuous side wall for defining said waist opening and providing said seat when unrestrained; and said first introduction and deployment means further comprises a first deployment catheter having a distal end segment, means for maintaining said first graft prosthesis in said collapsed state along said distal end segment during introduction and for releasing said first graft prosthesis, including means for restraining said coil spring in a collapsed elongated shape and means for releasing said coil spring to assume said expanded state.

26. The system of claim 24 wherein:

said waist opening stent is formed of first and second lengths of resilient coil springs attached to said continuous side wall for defining said waist opening and providing said seat when unrestrained; and said first introduction and deployment means further comprises a first deployment catheter having a distal end segment, means for maintaining said first graft prosthesis in said collapsed state along said distal end segment during introduction and for releasing said first graft prosthesis, including means for restraining said coil springs in a collapsed elongated shape and means for releasing said coil springs to assume said expanded state.

27. The system of claim 19 wherein:

said waist opening stent is formed of a resilient, ring-shaped coil spring attached to said continuous side wall for defining said waist opening and providing said seat when unrestrained; and said first introduction and deployment means further comprises a first deployment catheter having a distal end segment, means for maintaining said first graft prosthesis in said collapsed state along said distal end segment during introduction and for releasing said first graft prosthesis, including means for restraining said coil spring in a collapsed elongated shape and means for releasing said coil spring to assume said expanded state.

28. The system of claim 19 wherein:

said waist opening stent is formed of first and second lengths of resilient coil springs attached to said continuous side wall for defining said waist opening and providing said seat when unrestrained; and said first introduction and deployment means further comprises a first deployment catheter having a distal end segment, means for maintaining said first graft prosthesis in said collapsed state along said distal end segment during introduction and for releasing said first graft prosthesis, including means for restraining said coil springs in a collapsed elongated shape and means for releasing said coil springs to assume said expanded state.

\* \* \* \* \*